(12) United States Patent
Bruder et al.

(10) Patent No.: US 7,039,153 B2
(45) Date of Patent: May 2, 2006

(54) IMAGING TOMOGRAPHY DEVICE WITH AT LEAST TWO BEAM DETECTOR SYSTEMS, AND METHOD TO OPERATE SUCH A TOMOGRAPHY DEVICE

(75) Inventors: Herbert Bruder, Hoechstadt (DE); Arne Hoelzel, Wittenberg (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 32 days.

(21) Appl. No.: 10/763,116

(22) Filed: Jan. 22, 2004

(65) Prior Publication Data

US 2004/0213371 A1    Oct. 28, 2004

(30) Foreign Application Priority Data

Jan. 22, 2003    (DE) ............................ 103 02 567

(51) Int. Cl.
*G01N 23/00* (2006.01)

(52) U.S. Cl. ........................................................... 378/9
(58) Field of Classification Search ..................... 378/9
See application file for complete search history.

(56) References Cited

U.S. PATENT DOCUMENTS

| 4,196,352 A | 4/1980 | Berninger et al. |
| 4,284,895 A * | 8/1981 | Morgan et al. ................ 378/9 |
| 4,384,359 A | 5/1983 | Franke |
| 4,991,190 A | 2/1991 | Mori |
| 5,195,112 A | 3/1993 | Vincent et al. |
| 5,966,422 A | 10/1999 | Dafni et al. |
| 6,208,706 B1 * | 3/2001 | Campbell et al. ............... 378/9 |
| 6,421,412 B1 | 7/2002 | Hsieh et al. |

FOREIGN PATENT DOCUMENTS

WO    WO 02/26134    4/2002

OTHER PUBLICATIONS

"Efficient Object Scatter Correction Algorithm for Third and Fourth Generation CT Scanners," Ohnesorge et al, European Radiological Conference 1997, Published in Eur. Radiol. 9 (1999) pp. 563-569.

* cited by examiner

*Primary Examiner*—Craig E. Church
(74) *Attorney, Agent, or Firm*—Schiff Hardin LLP

(57) ABSTRACT

An imaging tomography apparatus, in particular x-ray computed tomography apparatus, for examining an examination subject has at least two acquisition systems, each having a radiator and a data acquisition unit to detect the radiation originating from the associated radiator. The acquisition systems are capable of rotating around a common rotation axis with a constant angular separation in the azimuthal direction. Radiation from only one of the radiators is permitted to reach the examination subject during the rotation of the acquisition systems. Signal contributions by the x-ray tubes not supplying this data acquisition unit with primary radiation arrive are prevented, the projection data set generated by one of the data acquisition units.

16 Claims, 5 Drawing Sheets

IMAGING TOMOGRAPHY DEVICE WITH AT LEAST TWO BEAM DETECTOR SYSTEMS, AND METHOD TO OPERATE SUCH A TOMOGRAPHY DEVICE

BACKGROUND OF THE INVENTION

1. Field of the Invention

The present invention concerns an imaging tomography apparatus and a method for operating such an apparatus, in particular an x-ray computed tomography apparatus, of the type having at least a first acquisition system, with a first radiator and a first data acquisition unit for detection of radiation originating from the first radiator, and a second acquisition system, with a second radiator and a second data acquisition unit for detection of radiation originating from the second radiator, wherein both acquisition systems are capable of rotating around a common rotation axis with a constant angular separation in the azimuthal direction.

2. Description of the Prior Art

Tomography apparatuses of the above type are known, for example, from U.S. Pat. Nos. 4,991,190, 4,384,359, 4,196,352, 5,966,422, and 6,421,412. An advantage that such tomography apparatuses with a multiple acquisition systems exhibit in comparison to an apparatus with one acquisition system is an increased data acquisition rate, which leads to a lower exposure time, and/or to an increased temporal resolution. A shortened exposure time is of advantage because with it, movement artifacts in the reconstructed image (for example, caused by voluntary and involuntary movements of the patient and/or by arrhythmias in the heart movement) are minimized. This is particularly of importance in the event a larger volume is scanned, for example by means of a spiral scan, for example of the heart. An increased temporal resolution is, for example, necessary for representation of movement cycles, because then the data used for reconstruction of an image must be acquired in the shortest possible time. Conventionally, this has been attempted to be achieved by increasing the rotation speed of the acquisition system, however the acceleration forces, and the mechanical problems resulting therefrom, increase significantly with additional rotation speed. Such problems can be solved with the cited tomography apparatuses, which have multiple acquisition systems (radiator-detector combinations) arranged separated from one another in the azimuthal direction, meaning angularly offset relative to one another. This type of tomography apparatus is particularly advantageous when spiral reconstruction algorithms are used for reconstruction of images from the raw data generated by the detectors, which only require projection data from an angular interval of 180°, because then, for example given the presence of two acquisition systems, the exposure time is reduced to a quarter of the measurement time required for a full rotation.

In x-ray computed tomography, unwanted artifacts can occur in the CT image if scattered x-ray quanta also reach the detector in addition to the primary quanta, due to x-ray quanta scattered in the examination subject. This is generally counteracted by scattered-ray collimators or scattered-ray grids that are positioned directly in front of the detector. The grids, fashioned from absorbing materials, have fine and suitably aligned channels that allow only the non-deflected (and thus image-relevant) x-ray quanta reach the detector, By enlarging the collimator height by an additional depth of the channels, the scattered-ray suppression could be improved, however this is at the cost of efficiency. Additionally, such an increase of the collimator height would be very difficult mechanically to control, and would in addition increase the costs for the detector system.

Numerous methods for scattered-ray correction are known, for example from the professional article by B. Ohnesorge, T. Flohr, K. Klingenbeck-Regn with the title "Efficient object scatter correction algorithm for third and fourth generation CT scanners", Eur. Radiol. 9, pages 563–569, 1999. Using a convolution model, the portion of the image intensity tracing back to the scatter radiation is determined, and is subtracted from the measured signal, and thus a signal largely traced back to the primary quanta is obtained.

SUMMARY OF THE INVENTION

An object of the invention is to improve the image quality in a tomography apparatus of the cited type.

This object is achieved according to the invention, in a tomography apparatus of the type initially described wherein, radiation from the respective radiators alternatively reach the examination subject during the rotation of the acquisition systems.

The invention thus concerns in particular tomography apparatus with two or more acquisition system that are arranged to acquire projection data from a number of different projection directions, and that in particular are fashioned to generate slice exposures and/or for 3D-scanning of the examination subject.

The invention is based on the recognition that, in a tomography apparatus with a number of acquisition systems, in particular in a multi-tube system, added scatter radiation artifacts can ensue since each detector would receive signals from both radiators ("cross talk") given simultaneous use of both radiators, in particular of both x-ray tubes. The invention also is based on the recognition that, for example given a two-tube system with two acquisition systems offset by 90° with scattered-ray collimators, no sufficient scattered-ray suppression can be achieved, because the quanta coming from one tube and scattered to the side at 90° have, with high probability, the same propagation as image-relevant primary quanta coming from the other tube, and thus are barely differentiable.

Numerous conventional methods for scattered-ray correction are applicable only with low efficiency, because the typical correction models created for a forwards scatter in a tomography apparatus would not suffice in a tomography apparatus with a number of acquisition systems.

In the tomography apparatus according to the invention, x-ray quanta from only an individual x-ray tube of the total number rotating x-ray tubes arrives at the examination subject, the quanta alternating, or being in succession, from tube-to-tube. This allows signal contributions by the x-ray tube(s) not supplying the data acquisition unit currently in use with primary radiation to be prevented in the projection data set generated by the respective data acquisition units.

The alternating irradiation preferably is accomplished by a control unit. This control unit can be a control unit as is present in conventional tomography apparatus for control of the rotation, the radiators and optionally the data acquisition units, that, however, is specially fashioned for realization of the inventive subject matter.

According to a preferred embodiment, the control unit is fashioned such that the radiators can be activated in alternation (or in succession if more than two radiators are present). For this, the control unit, for example, can operate the power supply devices associated with the radiators, in particular associated voltage generators.

According to another preferred embodiment, the control unit is fashioned such that the data acquisition units can be activated in alternation or in succession.

The control unit preferably is designed such that the data acquisition units can be synchronously activated with the respective associated radiators. Thus only radiation from the respective "correct" radiator is recorded and no scatter radiation from the radiators that are not directly active.

The control unit preferably is fashioned such that, from each of the acquisition systems, projection data can be generated in succession from a number of different projection directions, the projection data being generated alternately (successively) with the alternation of the irradiation of one of the acquisition systems. Thus an alternation of the irradiation is undertaken on a time scale that corresponds to the time scale of the acquisition of projection data from different directions.

In another embodiment, the alternation of the irradiation is accomplished by diaphragm devices that are controllable such that the radiators are gated in alternation (or in succession).

Alternation of the irradiation also can be realized by an image computer connected with the data acquisition units that is fashioned such that data generated by such a data acquisition unit whose associated radiator does not radiate directly at the examination subject are not used for image reconstruction.

The invention is also of advantage in a tomography apparatus with two or more acquisition systems with fan beam angles or measurement fields of different sizes from one another. In particular the maximum measurement fields scanned by the two acquisition systems given rotation around the rotation axis can be of different sizes. This can mean that the maximum fan angles of both acquisition systems are of different sizes. Alternatingly, the lengths of both detectors—measured in the azimuthal direction—can be of different sizes. In the medical examination of a patient, it is of particular advantage for the first measurement field to be able to scan the entire body cross-section of the patient and for the second measurement field be able to scan only a portion of the body cross-section, in particular the area of the heart.

In the tomography apparatus according to the invention both acquisition systems can be arranged in a common plane. This has the advantage that artifacts as a result of an unwanted movement of the patient (breathing, etc.) are minimized. However, embodiments are also possible in which the acquisition systems are separated from one another and/or can be positioned separated from one another in the direction of the rotation axis.

The cited object also is achieved according to the invention based in a method wherein the examination subject is irradiated in alternation or succession by radiation from the respective radiators during the rotation of the acquisition systems. In particular, only the irradiation from one of the radiators at a time is present.

The above-described advantages and preferred embodiments of the tomography apparatus according to the invention apply analogously to the method according to the invention.

According to a preferred embodiment of the method, the alternation or succession of the irradiation ensues multiple times during a rotation around the examination subject, The alternation ensues in particular with a period duration in the range of milliseconds or microseconds.

In another preferred embodiment, projection data from each of the acquisition systems are successively acquired from a number of different projection directions, the projection data being acquired by one of the acquisition systems alternating with the alternation of the irradiation.

The radiators likewise preferably are alternately activated.

According to a preferred embodiment of the method, the date acquisition units are alternately activated.

In particular, the data acquisition units can be activated alternately in synchronism with the respective associated radiator.

DESCRIPTION OF THE PREFERRED EMBODIMENTS

Three exemplary embodiments of a tomography device according to the invention are subsequently explained in detail in FIGS. 1 through 7. FIGS. 1 through 7 also serve to explain the method according to the invention.

Figure 1:
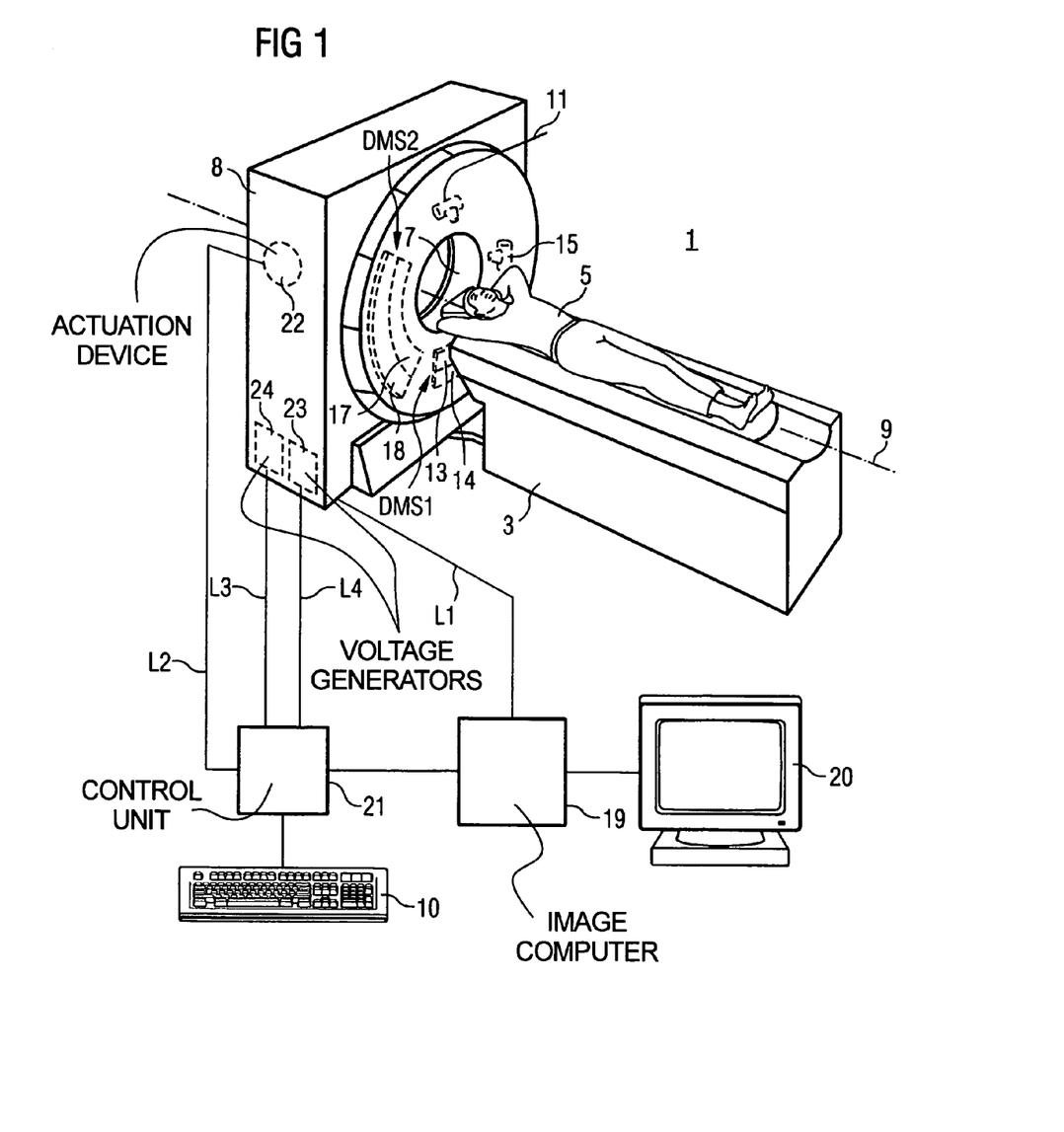
FIG. 1 illustrates a first exemplary embodiment of a tomography device according to the invention in a partial-perspective overall view, FIG. 2 show the two acquisition systems of the tomography apparatus of FIG. 1 in cross-section.

FIG. 1 shows a first exemplary embodiment of a tomography apparatus 1 (here an x-ray computed tomography apparatus) with an associated positioning device 3 for exposure and positioning of an examination subject 5, for example a patient. The patient 5 with the desired examination region or scan region can be inserted into an opening 7 (diameter 70 cm) in the housing 8 of the tomography apparatus 1 by means of a movable table top of the positioning device 3. Inside the housing 8, a gantry (not visible) is mounted so as to be rotated with high speed around a rotation axis 9 running through the patient. Moreover, for a spiral scan, a continuous axial feed is effected with the positioning device 3.

A control unit 10 is provided for operation of the tomography apparatus 1 by a doctor or an assistant.

To achieve a short scan time and/or a high temporal resolution, a number of acquisition systems, in the example two acquisition systems (n=2), are mounted on the gantry. A first acquisition system has an x-ray tube as a first radiator 11 and a first data acquisition unit DMS1 formed as an eight-line (eight-row) x-ray detector array as a first detector 13. A second acquisition system has a separate x-ray tube as a second radiator 15 and furthermore a second data acquisition unit DMS2 formed as a separate eight-line (eight-row) x-ray detector array as a second detector 17. The arrangement of the two radiators 11, 15 and the two detectors 13, 17 on the monitoring car is fixed during the operation of the tomography apparatus 1, such that their relative separations are also constant during operation.

The x-ray detector arrays are fashioned on a base of an electronically readable scintillator ceramic, known as a UFC ceramic. Surface detectors, for example with 256 or more lines, alternatively can be used. The electronic signals generated by the x-ray detector arrays are conditioned in respective downstream electronic data processing units 14 and 18 that, together with the respective associated detector 13 and 17, form the appertaining data acquisition units DMS1 and DMS2. In the data processing units 14 and 18, the electronic signals are integrated and optionally digitized. Each data processing unit 14 and 18 can include the following (not explicitly shown) components:

a) one integrator per detector element,
 b) a multiplexer downstream from the integrator,
 c) an electronic element downstream from the multiplexer for line-by-line readout and amplification of the signals from the individual detector elements,
 d) a downstream analog-digital converter, and
 e) an optional "Arithmetic Logic Unit" (ALU).

The thusly-obtained projection data of both quasi-continuously scanning acquisition systems are supplied via wiper rings or an optical transmission system to the stationary part of the gantry, and then to an image computer 19. In the image computer 19, they are processed using an image reconstruction algorithm into a CT image that can be displayed on a display device 20. The image computer 19 is fashioned such that the reconstruction of an image can be implemented using projection data or raw data of both acquisition systems. The projection data of both acquisition systems are thereby initially combined ("mixed") into a common projection data set or raw data set, taking their relative separation into consideration, The tomography apparatus 1 is controlled by a control unit 21 that is connected with the image computer 19 and with the operating unit 10. The control unit is also connected with the data processing units 14 and 18 via a data transmission line L1. Moreover, the control unit 21 operates (via a data transmission line L2) an actuating device 22 actuating the monitoring car, and operates (via data transmission lines L3, L4) two voltage generators 23, 24 that respectively supply the x-ray tubes with energy. The voltage generators 23, 24 are only indicated schematically, and at least some components thereof can be arranged on the gantry. In the normal case, the electrical energy is transferred to both x-ray tubes via wiper rings.

Figure 2:
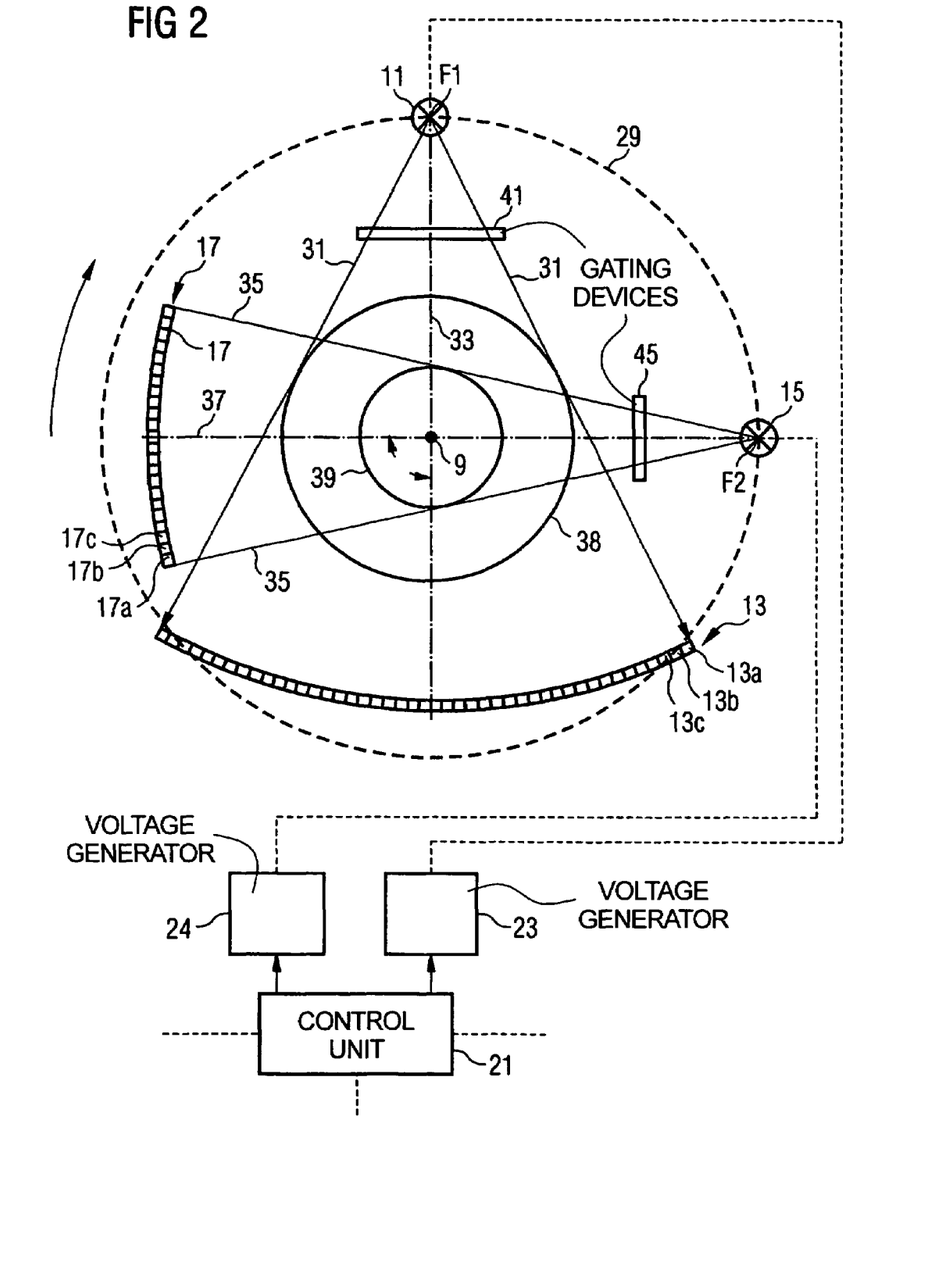

FIG. 2 shows both acquisition systems of FIG. 1 in detail. It is in particular shown how both radiators 11, 15 (and the focus F1 and focus F2) rotate in the arrow direction on a common rotation path 29 around the rotation axis 9 (which is perpendicular to the plane of the drawing) and alternately radiate x-ray fan beams that are respectively shown with edge rays 31 and 35 and a middle rays 33 and 37. During the respective radiation, raw data are generated from different projection angles for a subsequent image reconstruction. In the cross-section of FIG. 2, only one line of the respective detectors 13 and 17 (with respectively with a number of detector elements 13a, 13a, 13c and 17a, 17a, 17c, . . . ) is shown.

The lengths of each detector 13 and 17 is curved around the respective focus of the associated radiators 11 and 15, and are different, such that, in the representation of FIG. 2, detectable x-ray beams of different sizes arise for the two acquisition systems, and maximum measurement fields 38 and 29 of different sizes result.

To gate the x-ray beam from each radiator 11 and 15 in the direction of the rotation axis, thus also to select individual or multiple detector lines, a first gating device 41 is associated with the first acquisition system, and a second gating device 45 is associated with the second acquisition system, both tube-proximate. Each gating device 41, 45 can have two diaphragm plates that can be moved in a direction parallel to the rotation axis 9.

The azimuthal angular separation a of the acquisition systems is measured between the lines "focus-rotation center" (here identical to the middle rays 33 and 37 and is constant at least during an exposure for n, acquisition systems, and the angular separation preferably is substantially 360°/(2n), meaning, in the example of the Figures (n=2), substantially 90°, such that after 1/(2n) of a complete rotation (360°) an angular region of 180° is cumulatively scanned, which is sufficient for most image reconstruction algorithms. In the context of the invention, preferably a spiral reconstruction algorithm is used, that can operate with projection data of a half-rotation.

The control unit 21 acts on the voltage generators 23, 24 such that the tubes or radiators 11, 15 alternately radiate.

Figure 3:
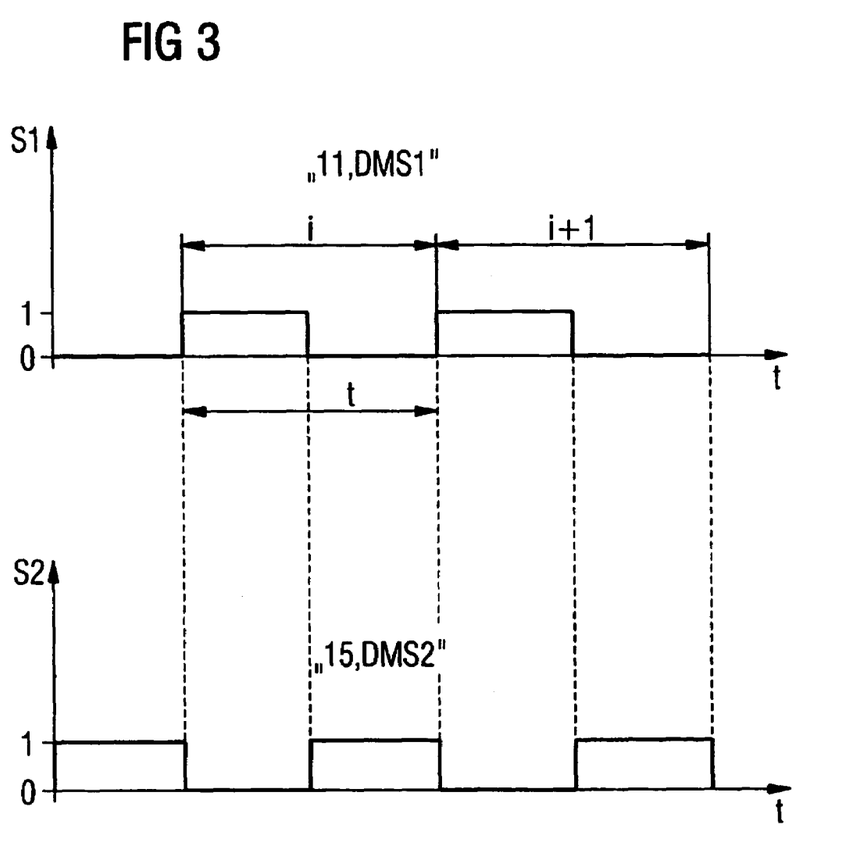
FIG. 3 is a time diagram to explain the control of the two acquisition systems of FIGS. 1 and 2.

In FIG. 3, the respective normalized curves over time t of the control signals S1 and S2, that ensure by the alternating operation, are shown for the first (upper curve) and the second (lower curve) acquisition system of FIGS. 1 and 2. During the rotation of the gantry, the control unit 21 alternately activates one of the two radiators 11, 15, which thus alternately radiate in a pulsed tube mode, Moreover, the control unit 21 switches the data acquisition units DMS1, DMS2 in phase or synchronously with the respective associated radiator 11, 15, When the first radiator 11 radiates, the associated first data acquisition unit DMS1 alone integrates the quanta striking its detector 13. Projection data acquired at the respective radiation time points—acquired at projection directions differing by 90°—together form a first measurement value set i that is read out. A second measurement value set i+1 is subsequently read out with the same alternation of the irradiation. During one rotation, approximately 100 to 1000 measurement value sets (typically 360) are acquired, such that a time interval Δt for a measurement value set amounts to approximately 1 msec.

During the radiation time of the second radiator 15, no radiation coming from the first radiator 11 is detected in the second detector 17, and vice versa. The detectors 13, 17 operate intermittently.

Figure 4:
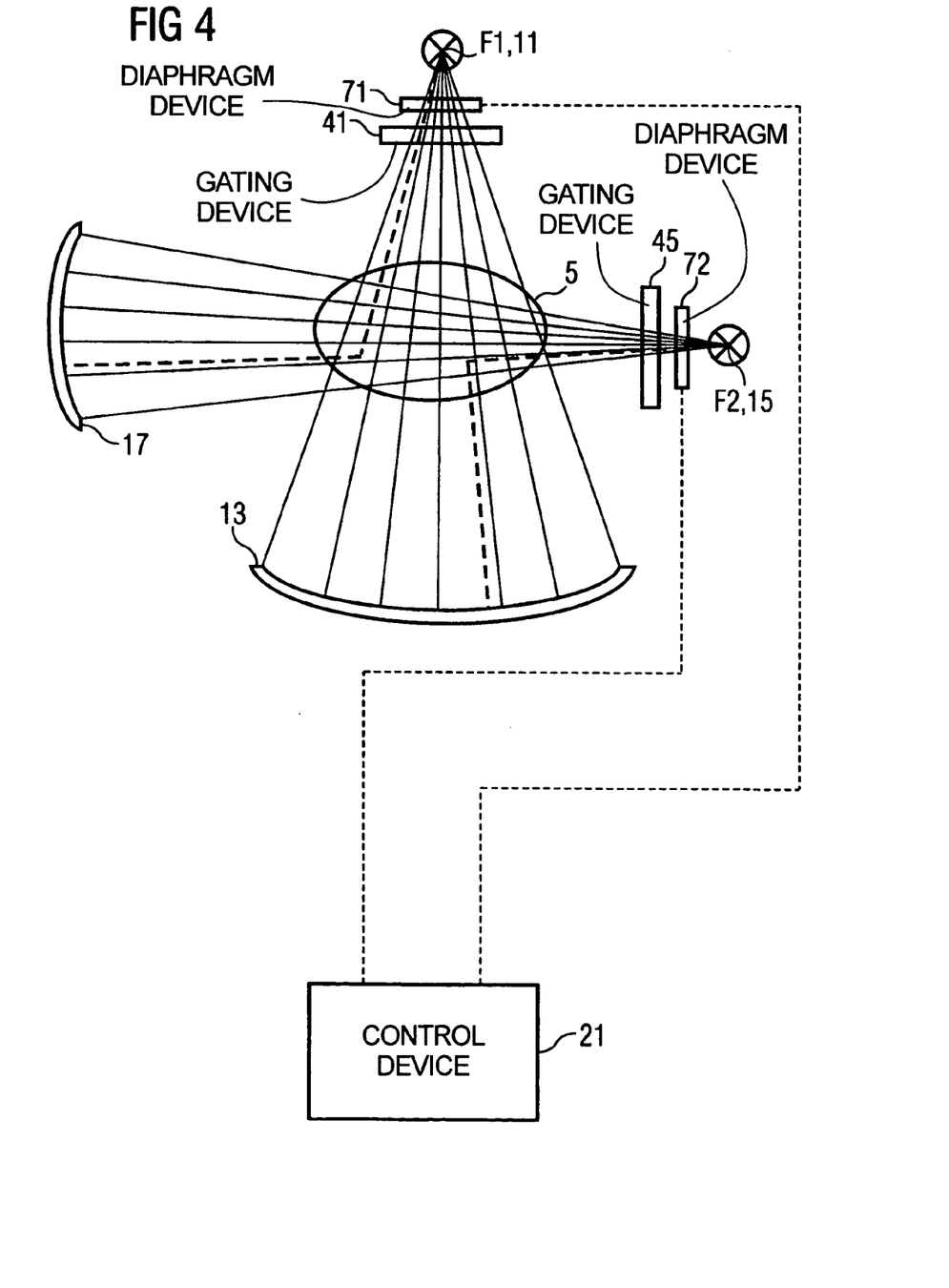
FIG. 4 shows the two acquisition systems of a tomography device according to the invention according to a second exemplary embodiment, in cross-section view.

Indicated in FIG. 4 with dashed lines are ray progressions of scattered x-ray quanta that are not interfering in the tomography device 1 because they only ensue when the detector 13 or 17 at which they arrive is not directly-supplied with primary x-ray quanta and is not detecting.

Additionally, in FIG. 4a second exemplary embodiment is shown that is largely identical to the first exemplary embodiment, but wherein contrast to the first embodiment, the control unit 21 does not act (for the alternating operation) via the voltage generators 23, 24 on the radiators 11, 15, but instead acts on the diaphragm devices 71, 72. These diaphragm devices 71, 72 are present, for example, in addition to the gating devices 41, 45, and alternately shift an absorber element in front of the radiator 11 or 15. In contrast to the first exemplary embodiment, the alternation of the irradiation thus does not ensue electrically in the framework of the power supply in the second exemplary embodiment, but rather mechanically. The radiators 11, 15 can continuously radiate.

Figure 5:
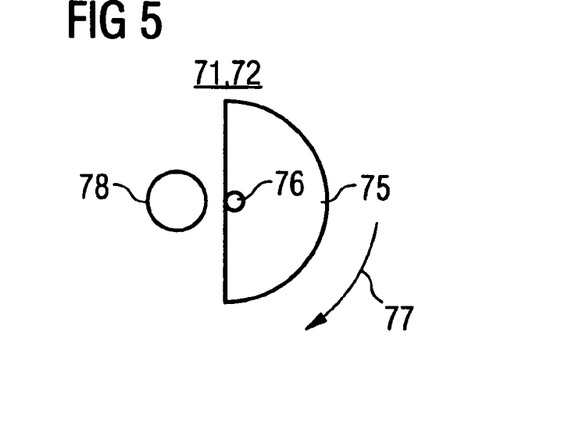
FIG. 5 shows details of the second exemplary embodiment pertaining to a diaphragm device, in a simplified view.

In FIG. 5, as a detail of the second exemplary embodiment, the assembly of the diaphragm devices 71, 72 is shown as a system with rotating absorber elements. The representation is in the viewing direction opposite to the radiation direction of the radiator 11 or 15. Each of the diaphragm devices 71, 72 has, as an absorber element, a disc 75 that is a sector of a circle (here a semicircle disc; generally the circumference is approximately 360°–360°/n) made of an x-ray-absorbing material. The disc 75 can be rotated very quickly in the arrow direction 77 around an axis 76 parallel to the radiation direction, such that a tube emission window 78 of the respective radiators 11 and 15 is alternately covered and not covered, and not covered and covered.

Figure 6:
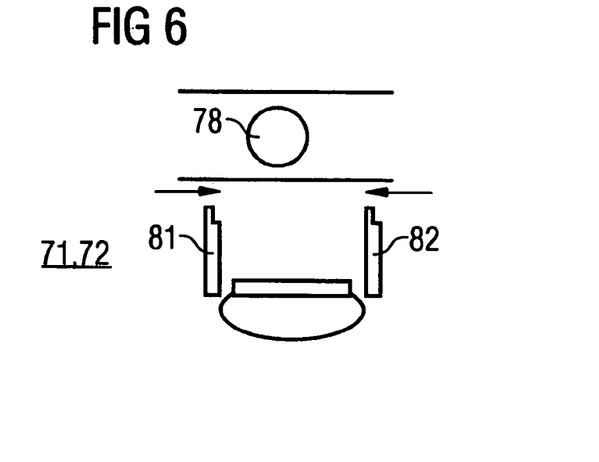
FIG. 6 shows details of a third exemplary embodiment pertaining to a diaphragm device according to the invention, in a simplified view.
Figure 7:
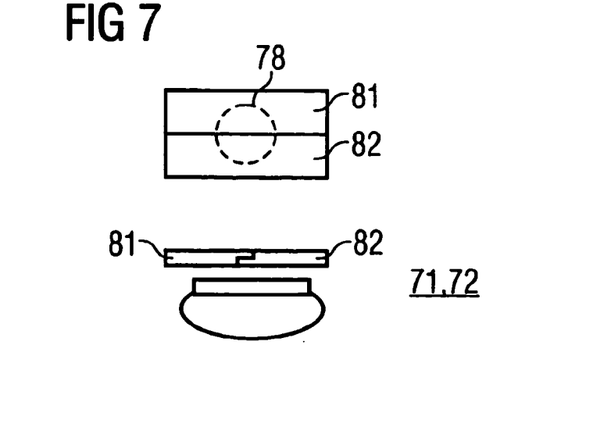
FIG. 7 shows the diaphragm device of FIG. 6 in a closed state.

In FIGS. 6 and 7, a third exemplary embodiment is shown in the same viewing direction (above) as in FIG. 5 and perpendicular thereto (below), in which the alternation of the irradiation likewise ensues mechanically. The third exemplary embodiment is largely identical with the second exemplary embodiment, but is different in the shown detail of the assembly of the diaphragm devices 71, 72. The shielding is arranged with venetian blind-like (jalousle-like) x-ray-absorbing absorber plates 81, 82. In FIG. 6, the diaphragm device 71, 72 is shown in the open state, in is shown in FIG. 7 in the closed state, respectively from two different viewing directions.

In the exemplary embodiment of the tomography apparatus 1 according to FIGS. 1 through 7, both acquisition systems (meaning in particular the respective connecting lines between radiator and detector, thus for example also the respective middle rays 23 and 27) are arranged in a common plane that is the plane of the drawing of FIGS. 2 and 4. In such an implementation, the CT device is particularly suitable for representation of movement cycles with high temporal resolution.

Although only tomography apparatuses with two acquisition systems are shown in the exemplary embodiments, the basis of the invention is also applicable to tomography apparatuses with three or more acquisition systems. The invention is, for example, applicable in the fields of medical technology and material examination, in particular baggage inspection.

Although modifications and changes may be suggested by those skilled in the art, it is the intention of the inventors to embody within the patent warranted hereon all changes and modifications as reasonably and property come within the scope of their contribution to the art.

We claim as our invention:

1. An imaging tomography apparatus comprising:
   a first data acquisition system comprising a first radiator that emits radiation in a first fan beam having a first maximum size, and a first data acquisition unit for detecting radiation in said first fan beam;
   a second data acquisition system, comprising a second radiator that emits radiation in a second fan beam having a second maximum size, different from said first maximum size, and a second data acquisition unit for detecting radiation in said second fan beam;
   a gantry at which said first and second data acquisition systems are mounted for rotating said first and second data acquisition systems around an examination subject and around a common rotation axis, with a constant angular separation between said first and second data acquisition systems in an azimuthal direction relative to said common rotation axis; and
   an arrangement for causing radiation from only one of said first and second radiators to reach said examination subject at a time, in alternation, during rotation of said first and second data acquisition systems.

2. An imaging tomography apparatus as claimed in claim 1 wherein said first radiator is a first x-ray radiator, said first detector is a first x-ray detector, said second radiator is a second x-ray radiator and said second detector is a second x-ray detector, and wherein each of said first and second data acquisition systems produces computed tomography projection data.

3. An imaging tomography apparatus as claimed in claim 1 wherein said arrangement comprises a control unit connected to each of said first and second data acquisition systems for operating said first and second data acquisition systems in alternation.

4. An imaging tomography apparatus as claimed in claim 3 wherein said control unit alternatingly activates said first and second radiators.

5. An imaging tomography apparatus as claimed in claim 3 wherein said control unit alternatingly activates said first and second data acquisition units.

6. An imaging tomography apparatus as claimed in claim 3 wherein said control unit activates said first and second data acquisition units respectively in synchronization with activation of the respective first and second radiators associated therewith.

7. An imaging tomography apparatus as claimed in claim 2 wherein said arrangement is a control unit connected to said first and second data acquisition systems, and wherein said control unit receives, from said first and second data acquisition systems projection data in succession from a plurality of different projection directions, said projection data being alternatingly generated by said first and second data acquisition systems during rotation around said examination subject.

8. An imaging tomography apparatus as claimed in claim 1 wherein said arrangement comprises a first diaphragm device for gating said radiation from said first radiator and a second diaphragm device for gating said radiation from said second radiator, said first and second diaphragm devices being operated to gate the respective radiation in alternation.

9. An imaging tomography apparatus as claimed in claim 1 wherein said arrangement comprises an image computer connected to said first and second data acquisition units, said image computer receiving raw data from each of said first and second data acquisition units and reconstructing an image from said raw data, said image computer using only said raw data from said first data acquisition unit acquired when said radiation from said first radiator irradiated said examination subject, and using only said raw data from said second data acquisition unit acquired while said radiation from said second radiator irradiated said examination subject.

10. A method for operating an imaging tomography apparatus comprising the steps of:
    rotating a first data acquisition system, having a first radiator and a first data acquisition unit, and a second data acquisition system, having a second radiator and a second data acquisition unit, around an examination subject, around a common rotation axis, and irradiating an examination subject with radiation emitted by said first radiator in a first measurement field having a first maximum size and with radiation emitted by said second radiator in a second measurement field having a second maximum size different from said first maximum size, while maintaining a constant angular separation between said first and second data acquisition systems in an azimuthal direction relative to said common rotation axis; and
    operating said first and second data acquisition systems to irradiate said examination subject with radiation from only one of said first and second data acquisition systems at a time, in alternation, during rotation of said first and second data acquisition systems.

11. A method as claimed in claim 10 comprising alternating irradiation of said examination subject multiple times during each rotation of said first and second data acquisition systems around said examination subject.

12. A method as claimed in claim 10 wherein said first radiator is a first x-ray radiator, said first data acquisition unit is a first x-ray detector, said second radiator is a second x-ray radiator and said second data acquisition unit is a second x-ray detector, and comprising obtaining projection data from examination subject with said first and second data acquisition systems and reconstructing a computed tomography image from said projection data.

13. A method as claimed in claim 12 comprising successively acquiring said projection data with each of said first and second data acquisition system from a plurality of different projection directions, and acquiring said projection data in alternation corresponding to the alternation of the irradiation of the examination subject.

14. A method as claimed in claim 12 comprising alternating irradiating said examination subject by alternatingly activating said first and second radiators.

15. A method as claimed in claim 12 comprising alternatingly activating said first and second data acquisition units.

16. A method as claimed in claim 15 comprising alternatingly activating said first and second data acquisition units synchronized with alternating activation of said first and second radiators.

* * * * *